United States Patent [19]

Watt

[11] Patent Number: 4,554,916

[45] Date of Patent: Nov. 26, 1985

[54] ROTARY PROPORTIONING INHALATOR

[76] Inventor: James Watt, 211 W. 56th St., Suite 18M, New York, N.Y. 10019

[21] Appl. No.: 517,846

[22] Filed: Jul. 27, 1983

[51] Int. Cl.$^4$ ............................................. A61M 16/00
[52] U.S. Cl. ............................ 128/203.12; 128/200.19; 128/204.26; 137/625.41
[58] Field of Search ........................ 128/203.25, 203.12, 128/205.24, 200.19, 206.24, 206.26, 205.25, 203.27, 203.26, 204.17, 204.25; 137/625.41, 625.4

[56] References Cited

U.S. PATENT DOCUMENTS

| | | | |
|---|---|---|---|
| 1,090,863 | 3/1914 | Kelley | 128/200.19 |
| 1,695,930 | 12/1928 | Schroder | 128/203.25 |
| 1,702,982 | 2/1929 | Schroder | 128/203.25 |
| 2,625,155 | 1/1953 | Engelder | 128/206.24 |
| 2,666,432 | 1/1954 | Stanton | 128/206.26 |
| 3,506,003 | 4/1970 | Gregory | 128/203.27 |
| 3,893,458 | 1/1975 | Fletcher et al. | 128/204.25 |

Primary Examiner—Henry J. Recla
Attorney, Agent, or Firm—Kenyon & Kenyon

[57] ABSTRACT

A therapeutic inhalator variably proportions and mixes a plurality of pressurized therapeutic gases at a high volume flow and supplies them on a demand basis rate to a patient from a mixing chamber inside a body of generally cylindrical configuration. Gases, such as carbon dioxide, oxygen, and nitrous oxide, are delivered from separate supply circuits to separate demand valves. Demand valves located at the inlet portals of the inhalator body are capable of delivering gas to the mixing chamber when unblocked by an aperture in the wall of the mixing chamber which acts as a proportioning member by regulating which of the inlet portals are coupled to the mixing chamber and what extent each portal is exposed. There are one or more apertures in the proportionary member. The mixing chamber communicates the mixed gases to the patient via a widemouthed opening which fits over the nose and mouth. Each demand valve which is actively coupled to the mixing chamber admits gas thereto in response to a drop in pressure at a predetermined level in the mixing chamber as a result of the patient's inhalation. Selection and proportioning of gases supplied to the mixing chamber is accomplished by changing the position of the proportioning member.

29 Claims, 15 Drawing Figures

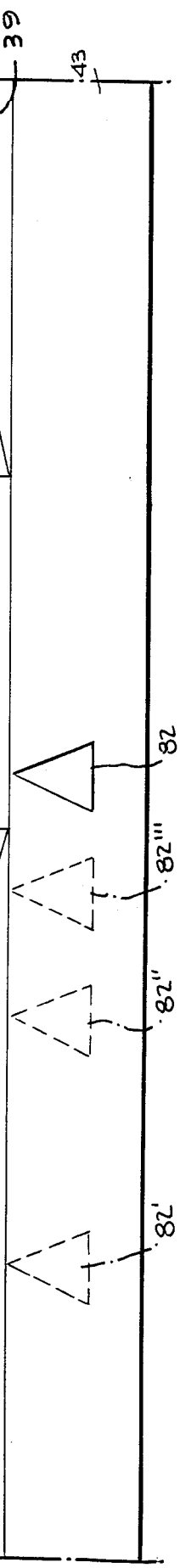
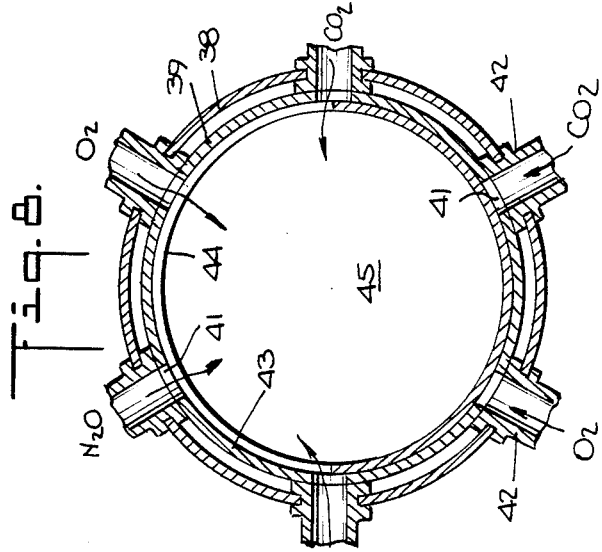
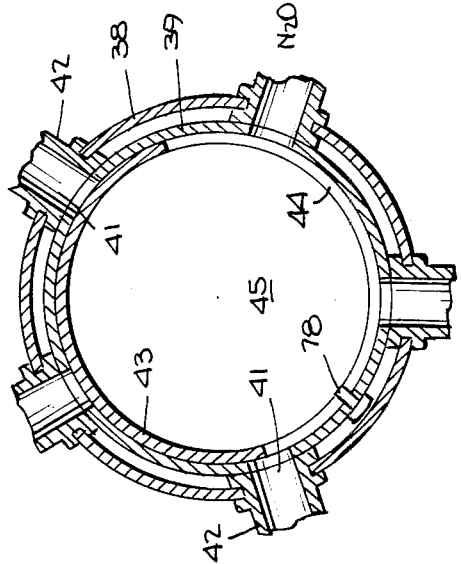
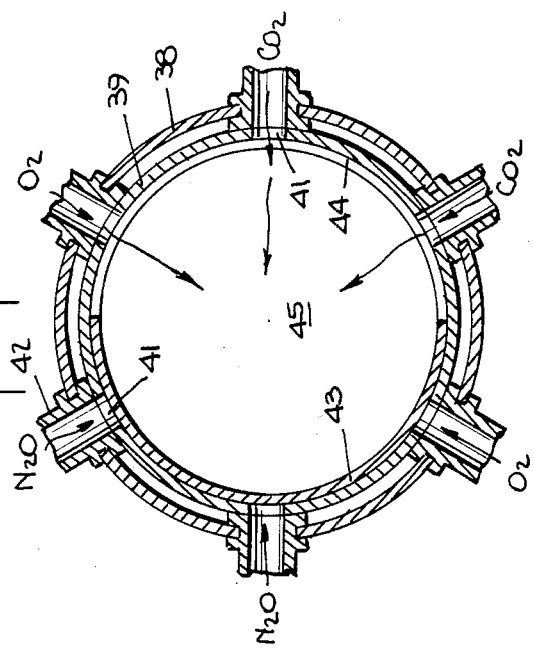

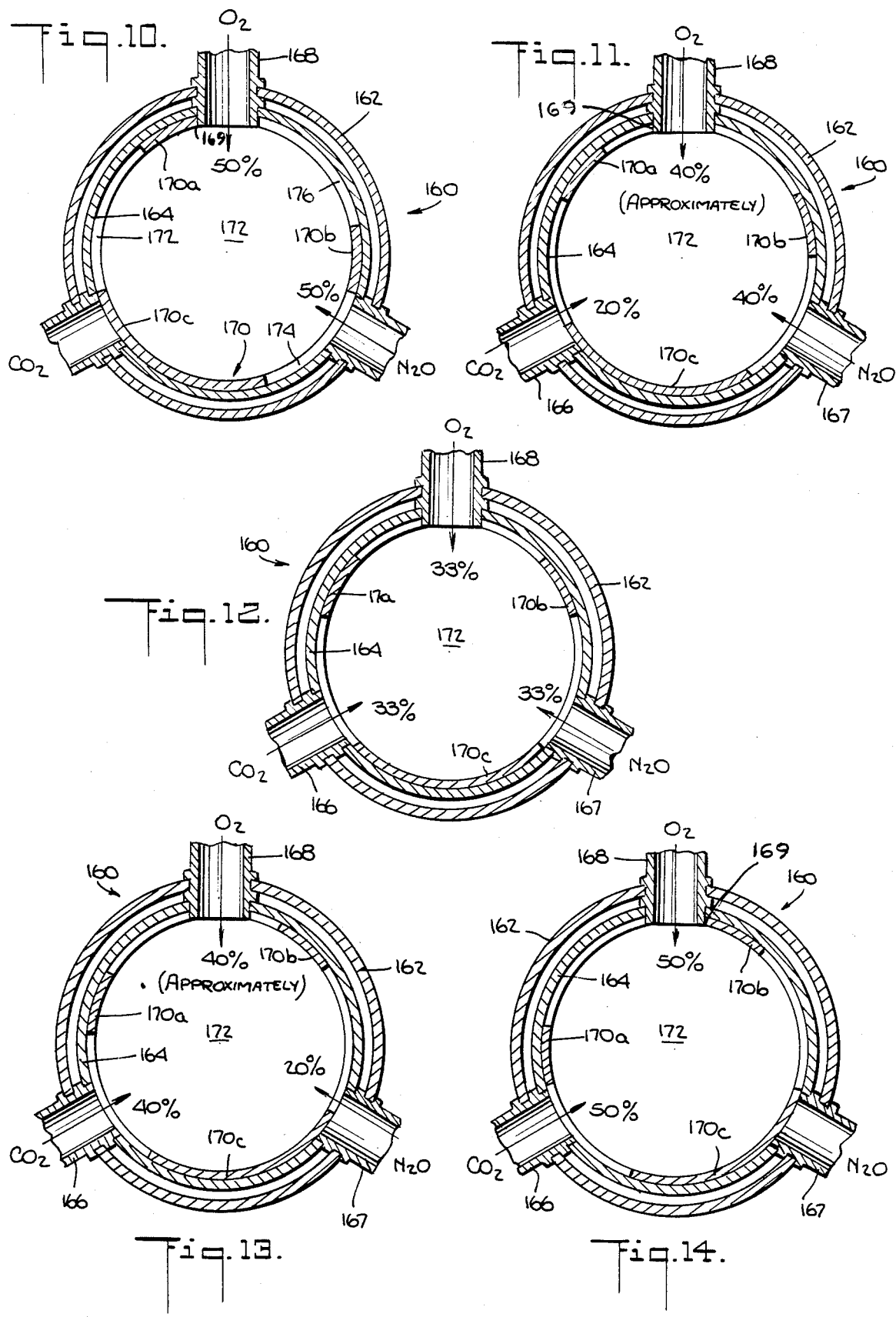

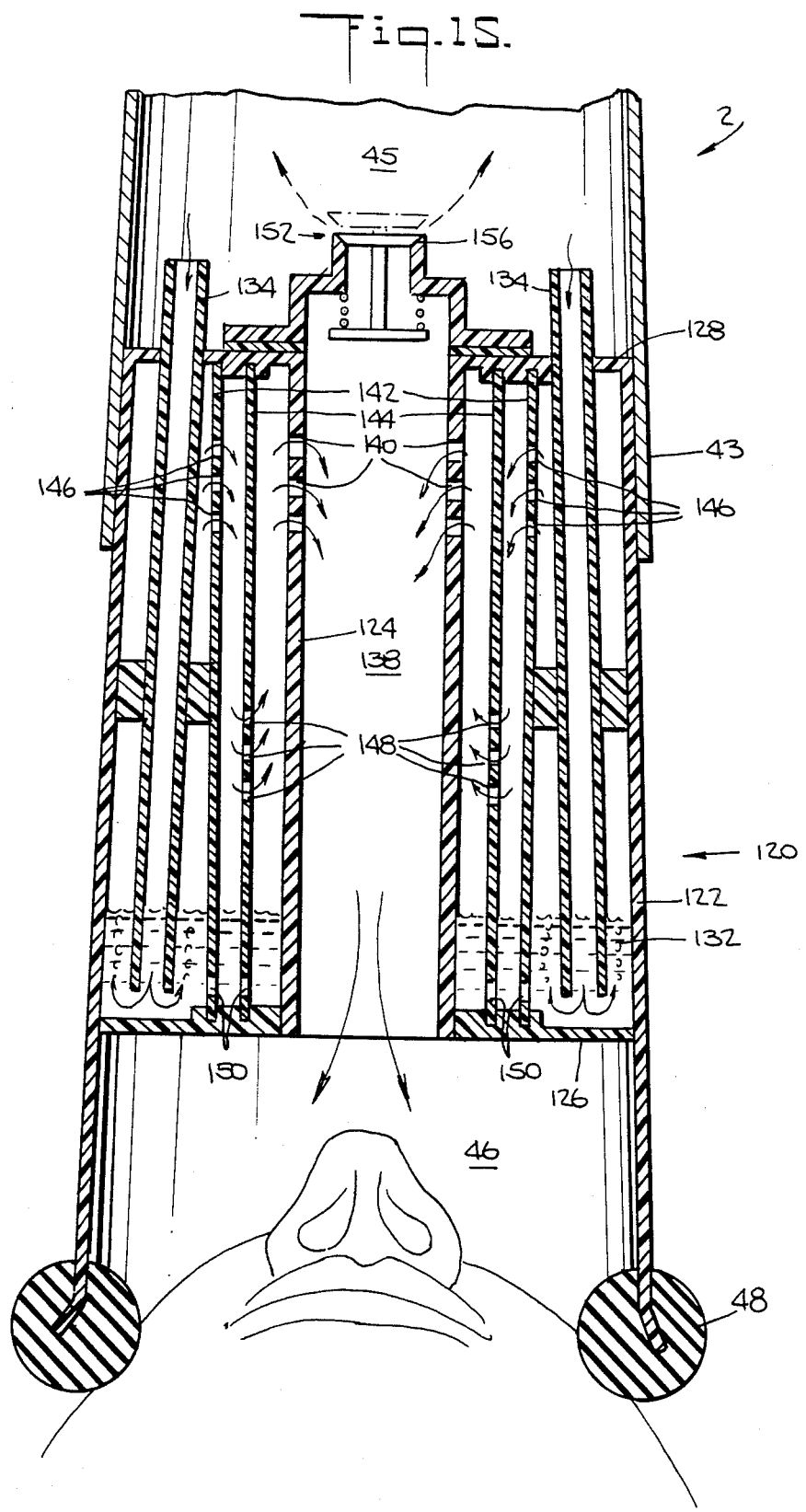

ROTARY PROPORTIONING INHALATOR

BACKGROUND OF THE INVENTION

This invention relates to a rotary gas proportioning inhalator which provides accurate, variable proportioning of a plurality of pressurized gases at a high rate of flow on a demand basis, while permitting the level of one gas to be maintained at a constant or adequate level.

Practical use of the inhalator of the invention is to further the art of administering carbon dioxide, oxygen and nitrous oxide to patients suffering from psychoneurosis. Carbon dioxide therapy is also beneficial for facilitating the recovery of speech in stroke victims and as an adjunctive thereapy for allergy, drug addiction and alcoholism. Finally, carbon dioxide may be used to enhance the creative process and promote greater self-realization.

In 1929 Loevenhart, Lorenz and Waters found that 30–40% carbon dioxide in oxygen enhanced mental clarity in catatonic patients for short periods of time. In 1947, L. J. Meduna used 20–30% carbon dioxide in oxygen as a neurophysiological therapy for treating psychoneurosis without psychotherapy. Meduna theorized that carbon dioxide cures psychoneurotic conditions through repeated administration of carbon dioxide thereby increasing the threshold of stimulation of reverberating neurotic circuits and achieving homeostasis by turning positive feed back systems into negative feed back systems. In 1952, Moriarty confirmed that carbon dioxide inhalation therapy was beneficial for anxiety states, phobic reactions, character disorders, migrane, alcoholism and psychosomatic conditions such as spastic colitis. Moriarty also maintained that carbon dioxide therapy works by breaking up pathological reverberating neural circuits to allow homeostatic mechanisms to reestablish themselves. He also believed that carbon dioxide therapy facilitates the psychotherapeutic process by releasing emotional tension through emotional discharge and by enhancing the accessibility of unconscious material.

To supply the gases to the patient, Meduna used a single cylinder having a fixed ratio of gases (up to 30% carbon dioxide in oxygen) which was connected by a long hose, through a large eleven liter rebreathing bag and thence, by a short tube to a face mask. When the cylinder was opened, it flowed at a constant rate into the rebreathing bag. When the patient breathed through the face mask, the rebreathing bag contracted and expanded as it lay on the patient's chest. Disadvantages of this system included inability to vary the gas mixture, inability to mix in nitrous oxide to enhance induction, the nuisance of the rebreathing bag, the variability of the gas mixture due to increases in carbon dioxide level with exhalation, and the difficulty of cleaning the rebreathing bag after each usage.

Moriarty utilized a system having three different cylinders (carbon dioxide, oxygen and nitrous oxide), with the flow of each being regulated by a separate flow meter having a manual wheel control and a visual meter. A double Y system of connected hoses brought the gases to the rebreathing bag and thence to a face mask similar to that used by Meduna. Some disadvantages of this arrangement are that all three flow meters must be regulated simultaneously to control gas proportions, that the resulting gas proportions are not precise, and that a rebreathing bag is required.

A gas mixture proportioner for a plurality of gases is described in U.S. Pat. No. 3,515,155, to Haffner et al., in which each supply line leading from one of the gas sources to a common mixing chamber contains a plurality of metering valves of different capacities connected in parallel. Gas from the mixing chamber can be fed, for example, to a diver. By using different combinations of valve size, e.g. by closing some, the rate of flow through each line is controlled to arrive at desired proportions of gas in the mixing chamber. In this system, gases mixed in the mixing chamber are fed either directly to a reducing valve and thence to the diver, or indirectly to the diver through an accumulator tank. This system is complex and costly.

U.S. Pat. No. 3,800,830, to Etter, shows a valve for selectively metering or mixing liquids or gases via apertures in a number of disk-like valve elements. The disks are stacked and connected to a common shaft. Each disk can be rotated to an off position or to an in-between position at which one or more apertures carried in skirts attached to the disks are positioned to pass gas, from a central space adjacent to the disk to which a particular gas is supplied, to an outlet line which is coupled to a manifold. This device, while providing control by each disk of admission of an individual gas to the mixing manifold, does not provide a reserve which will accommodate high volume flow on a demand basis and does not provide interrelated control of the gas proportions in the mixture.

In the mixing valve of U.S. Pat. No. 4,156,438, to Keisow, pairs of tapered movable metering openings are carried in a metering member, each tapered opening being associated with one of two gases to be mixed. A bore on the opposite side of the tapered slot collects and mixes the output. Motion of the member in which the tapered slots are carried causes more or less of one or the other of the gases to pass through into the collector. The two gases supplied are mixed in inverse proportion to each other, i.e., the percentage of one gas can be varied from zero to 100% at the same time that the percentage of other gas is varied from 100 to 0%. However this valve is not capable of proportioning three gases upon demand, nor is it capable of maintaining constant the proportion of one gas, such as oxygen, while the proportions of the other gases are varied.

It is an object of the present invention to provide an inhalator for supplying a proportioned mixture of a plurality of gases from pressurized sources to a patient while providing a high volume of flow on demand.

It is still another object of the invention to provide an inhalator arrangement in which three different gases, such as carbon dioxide, oxygen and nitrous oxide are received from separate sources at the same pressure and are mixed, so as to provide a constant or adequate level of oxygen at all times for life support while the proportion of the other two gases are variable with one adjustment by the operator.

It is a further object of the invention to provide an inhalator which is of a suitable structure for direct application to the face of a patient.

SUMMARY OF THE INVENTION

The above problems are resolved by a rotary proportioning inhalator which has an input system composed of a plurality of gas supply circuits, each circuit extending from a separate gas source to an individual demand valve. Each demand valve has an outlet which is connected, through a wall of the inhalator and optionally connects through at least one control aperture in a proportioning control member, into a mixing space within the inhalator.

The inhalator includes two nested bodies of a generally cylindrical configuration. The outer body of the inhalator, which is comprised of an outer cylinder and a middle cylinder, has a plurality of inlet portals located peripherally around its curved surface; each portal is provided with an adapter into which the outlet of a demand valve is received. An inner body or cylinder provides a central space or mixing chamber and has one or more proportioning control apertures, constituting the proportioning control member. The inner body or cylinder has a single large opening at its base into which a transparent tubular face cushion adapter is fitted. The transparent adapter carries an inflatable face cushion which can be placed over the nose and mouth of a patient. The two cylindrical bodies can be manually rotated relative to each other so that selected inlet portals remain in simultaneous communication with the mixing chamber through one or more proportion-regulating apertures to permit the simultaneous intake of gas into the mixing chamber for delivery to the patient, upon respiratory demand, via the demand valves from various input gas circuits.

The respiratory demand of the patient during insperation produces negative pressure in the mixing chamber causing all unobstructed demand valves to operate and feed gas into the mixing chamber and from there to the patient. Each of the demand valves is set to respond to the same level of negative pressure and, when exposed via a regulating aperture, opens and feeds gas into the mixing chamber. To raise the moisture content of dry bottled gases supplied to the inhalator, a transparent humidifier having a low impedance to the flow of gases can be fitted in place of the transparent tubular adapter.

The rotary proportioning inhalator is peferably supported during use by suspending it over the patient from an adjustable boom and support pole and, along with the assembled gas supply cylinders can be moved about on a wheeled carriage.

BRIEF DESCRIPTION OF THE DRAWINGS

FIG. 6 is a view of a mixture indicator useful with the proportioning inhalator of FIG. 2.

FIGS. 7 and 8 are views, in cross-section, of the six portal mixing chamber of FIG. 2, showing the proportion-regulating aperture in two different positions.

FIG. 9 is a view, in cross-section, of a mixing chamber having five portals.

FIGS. 10–14 are views in cross-section, of an embodiment of a rotary inhalator having three inlet portals and three regulating apertures.

FIG. 15 is a view, in vertical cross-section, of a humidifying chamber useful with the inhalator of the invention.

DETAILED DESCRIPTION OF THE INVENTION

Figure 1:
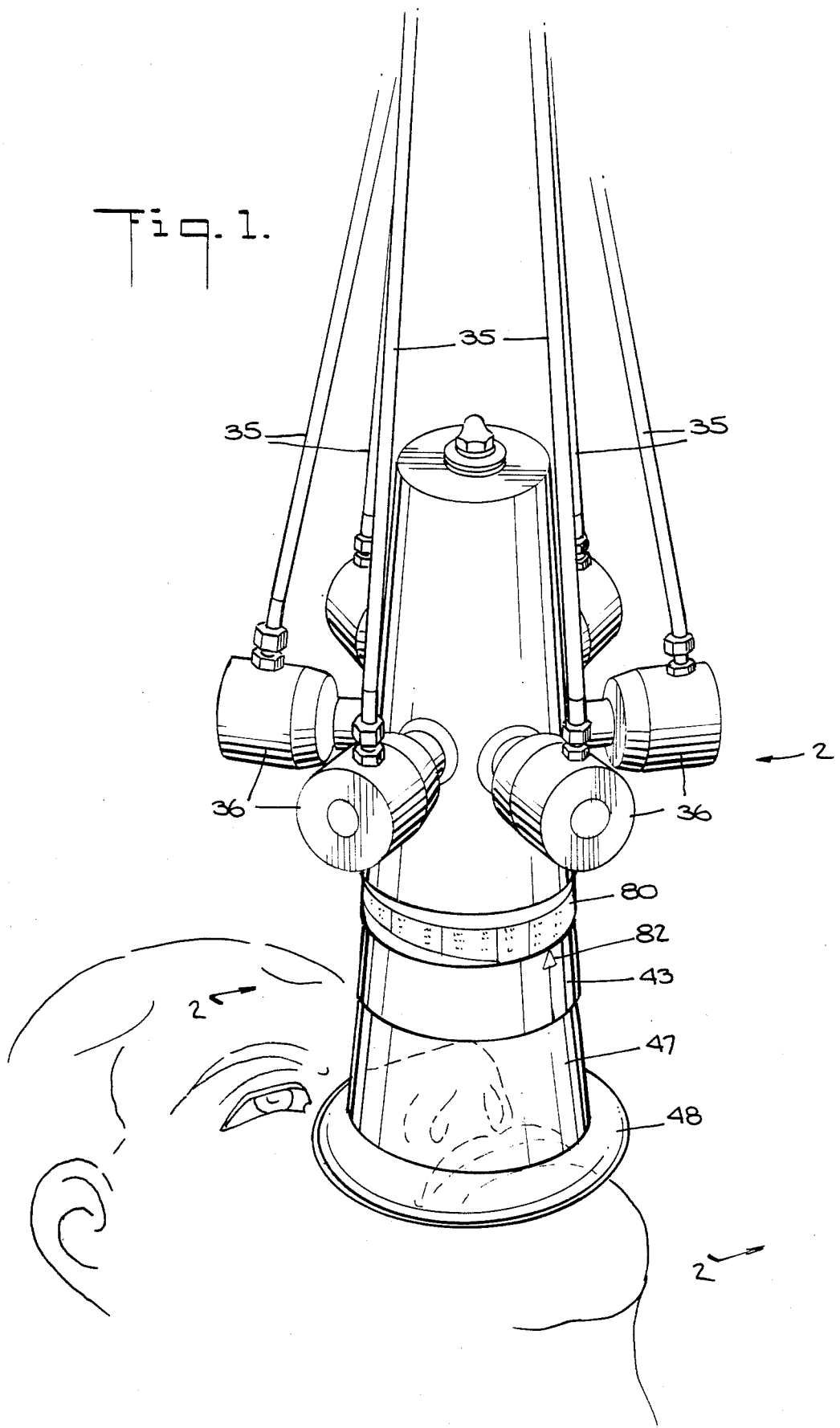
FIG. 1 is a perspective view of a rotary proportioning valve according to the invention, showing the multiple demand valve input circuits, the tubular face adapter and the inflatable face cushion.

FIGS. 1 to 4 show an inhalation apparatus which includes an inhalator 2 having a gas input system with six parallel gas supply circuits 3. Each gas circuit 3 (FIG. 4) includes a therapeutic gas source in the form of a pressurized supply cylinder 31, a cylinder pressure gage 32, a cylinder outlet pressure regulating valve 33, an outlet pressure gage 34, and a length of rubber high pressure hose 35 which terminates at the input of demand responsive valve 36. Each demand valve 36 has an outlet nipple 10 (FIG. 2) which fits into an adapter sleeve 42 mounted on inhalator 2. Each valve 36 is provided with one or more outlet ports (not shown) for expiration of gas during exhalation. The demand valves may be of a type which is well known in the art such as Part No. 900-002-063, made by the Robertshaw-Fulton Controls Company, Anaheim Division, Anaheim, Calif.

Inhalator 2, a rotary proportioning demand valve, is suspended from a mobile suspension boom stand 160 (FIG. 3), which has a metal carriage platform 162 for gas cylinders 31. Carriage platform 162 is movably supported on casters 164. Carriage platform 162 has six recessed circular areas (not shown) on its upper surface which receive the bottoms of the gas cylinders. Carriage platform 162 also supports an extendable vertical support pole 166 comprised of two lockable telescoping tubular sections. At its upper end, the support pole plugs into boom position adjuster 168. Locking screw 170 sets the angle on boom adjuster 168, setting the position of tubular boom assembly 172. Boom 174 and boom end angle bracket 176 support the run of gas feed hoses 35 from cylinders 31 to inhalator 2. The latter depends from the end of angle bracket 176, being supported by the ends of hoses 35 or, if desired, by a cable (not shown).

Figure 2:
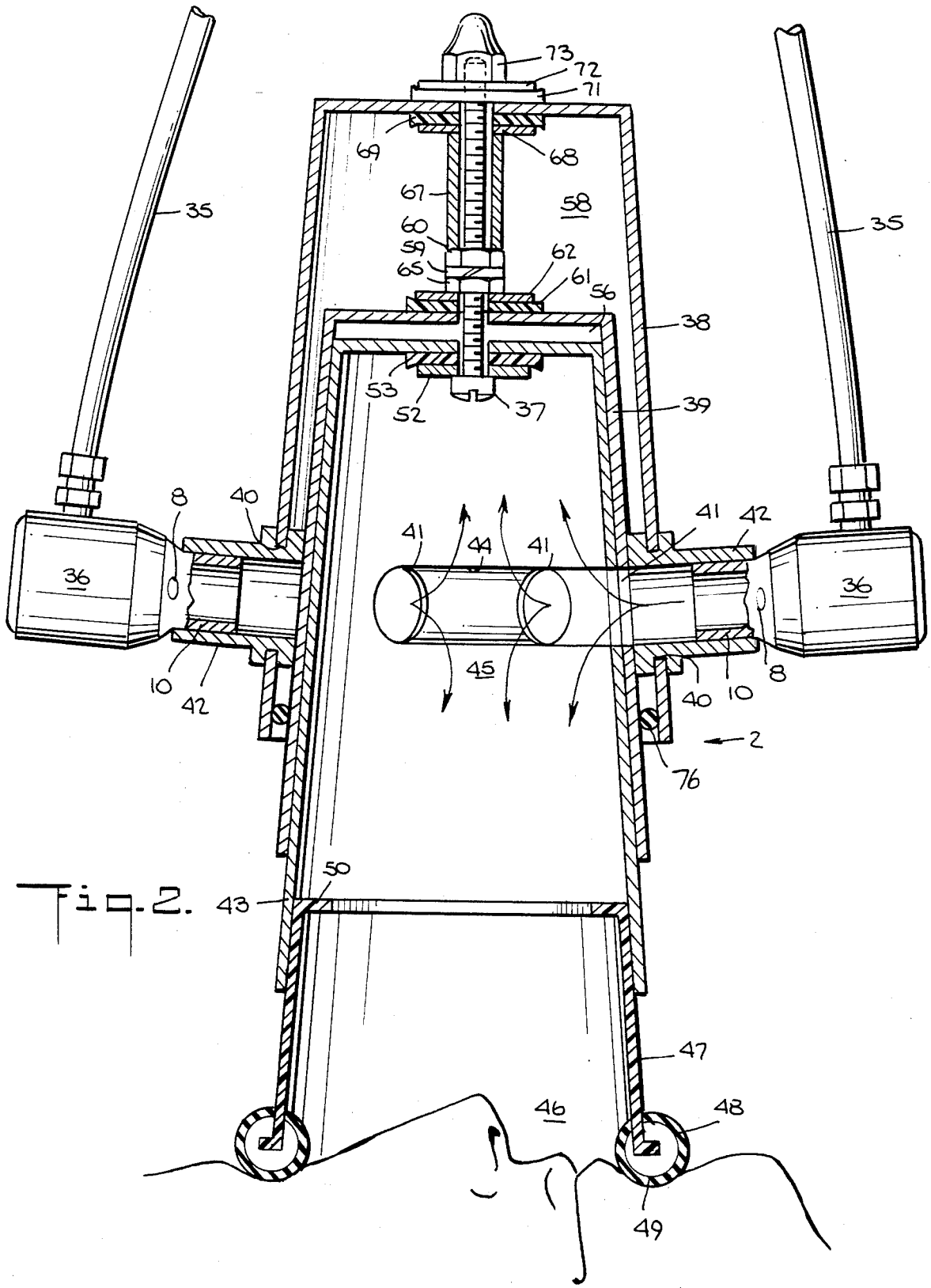
FIG. 2 is an elevation view, partially in section, of the rotary proportioning valve of FIG. 1, showing the manner of assembly and four out of six inlet portals.

As can be seen in FIG. 2, inhalator 2 includes an inhalator body formed of two hollow, flat-topped, open-based, concentrically mounted, somewhat conical cylinders, e.g. outer cylinder 38 and middle cylinder 39. Each of these cylinders is provided with six circular portals; outer cylinder inlet portals 40 in outer cylinder 38 are slightly larger in diameter than inlet portals 41 in middle cylinder 39. Pairs of inlet portals 40 and 41 are regularly disposed around the curved surfaces of the cylinders, with their centers lying in a plane which is parallel to the cylinder bases. As seen in FIG. 2, portals 40 of the outer cylinder are located one-third of the way up from the open base of middle cylinder 39. The portals in each pair are maintained in fixed position relative to each other by means of tubular demand valve inlet adapters 42 which are emplaced orthogonal to the walls of the cylinders, each one passing through the respective outer cylinder inlet portal 40 into a tight, peri-portal abutment on the outside of the adjacent middle cylinder inlet portals 41. The two concentric cylinders are spaced slightly apart from each other by means of an O-ring or gasket 76 and are maintained in place in the nested configuration by coaxial bolt 37.

The rotary valve of the inhalator has a flat-topped, open-based, slightly conical inner cylinder 43 which is conformably nested inside of middle cylinder 39 and which is rotatably supported on coaxial bolt 37. The space within inner cylinder 43 defines mixing space 45. An elongate proportion-regulating aperture 44 lies approximately two-thirds of the way up the wall of cylinder 43 from the base opening, being in line with middle cylinder inlet portals 41 and extending half-way around the circumference. By turning inner cylinder 43 on the axis provided by bolt 37, the proportions of gas supplied from demand valves 36 to central mixing space 45 can be controlled. The contents of mixing chamber 45 are made available to the patient through the wide, low impedance opening in the bottom of mixing chamber 45 and may be coupled to the patient via face opening 46 in detachable, transparent, plastic, tubular face adapter 47. Face opening 46 is surrounded by an inflatable doughnut or face cushion 48 which may be made of rubber and which is conveniently attached to lower flange 49 on face adapter 47. Inward-turned flange 50 provides structural strength to the face adapter at its top.

Axial bolt 37, together with a number of nuts and washers, holds outer, middle, and inner conical cylinders 38, 39 and 43 in position and provides pneumatic isolation while permitting rotation of the inner cylinder relative to the cylinders of the outer body. From below and moving upward, axial bolt 37 passes through inner cylinder retaining washer 52 and inner cylinder pneumatic seal washer 53, and then through successive holes in inner cylinder 43 and middle cylinder 39. From cylinder 39, the bolt passes through middle cylinder sealing washer 61, washer 62, and then into nut 65. The washer pairs 52 and 53, 61 and 62 prevent travel of gases from mixing chamber 45 to inter-cylinder spaces 56 and 58, respectively. By adjustment of nut 65 and, thus, of the length of bolt 37 beneath it, inner cylinder 43 can be snugly nested in middle cylinder 39, while permitting rotation of the two cylinders relative to each other. Lock nut 60 and lock washer 59 insure the maintenance of a fixed distance between the two inner cylinders. Tubular extension sleeve 67, supported on nut 60, spaces the middle and the outer cylinders. The upper end of sleeve 67 supports washer 68 and upper sealing washer 69 against the inner surface of outer cylinder 38. The axial bolt 37 passes through a hole in cylinder 38. On the outside of cylinder 38, the bolt passes through outside pneumatic seal washer 71, retaining washer 72, and into retaining nut 73. By means of the bolt and nut assembly just described, the degree of friction between the outer cylinder assembly and inner cylinder 43 is made adjustable while a reliable hermetic seal is insured. At the same time, easy disassembly and cleaning is provided.

As previously mentioned, additional structural support and pneumatic sealing is provided by O-ring 76 which is placed around and near the bottom of middle cylinder 39 and is in contact with the skirt of outer cylinder 38. The tight conjunctions of the O-ring and of the rubber demand valve adapters 42 lock outer cylinder 38 and middle cylinder 39 together in a single body, preventing their rotation with respect to each other.

In its function as a rotary proportioning control element, inner cylinder 43 is provided with regulating aperture 44 which extends circumferentially part way around the cylinder. In the embodiment of FIGS. 7 and 8, aperture 44 extends halfway around the cylinder so that three or four of the six demand valves are exposed at one time to the negative pressure in the mixing chamber. Since all of the demand valves are set to respond to the same demand pressure in the mixing space, each valve which is exposed through the aperture will release gas simultaneously with the other exposed valves when the pressure in the space drops below the predetermined level. The six inlet portals, spaced equally around the circumference, are provided with gas from cylinders 31 as follows. Two adjacent portals are fed nitrous oxide ($N_2O$). Adjacent portals on either side of the first pair are fed oxygen ($O_2$). The remaining pair of portals is fed carbon dioxide ($CO_2$). Thus, the positioning of inner cylinder 43 at any point around the inside of the inhalator outer body assembly permits oxygen always to be available and a range of mixtures as shown in FIG. 6 to be obtained.

On the indicator dial of FIG. 6, inner cylinder 43 can be seen to be rotatable through the full 360° with respect to the middle cylinder 39 to control gas mixture. Rotation of pointer 82 through 90° to the left, relative to indicator dial 80 on middle cylinder 39, produces a variation of $N_2O$ going from 66% to 0%, while at the same time, carbon dioxide, is added to the mixture in the reverse proportion of 0% to 66%. The oxygen in the mixture remains constant at a life-supporting 33%. Should one oxygen supply cylinder become exhausted while a patient is being treated, the operator can switch immediately to a full one in the other oxygen circuit by rotating the valve pointer to the other half of scale 80, which is 180° opposite. To assist the operator in the latter circumstance and to insure an adequate supply of oxygen, a commercially available low pressure alarm (not shown) can be put on the pressure reducing manifold of each oxygen cylinder.

Indicator dial 80 and pointer 82 are juxtaposed to one another on the outside surfaces of middle cylinder 39 and inside cylinder 43, respectively, and give an indication of the mixture being provided by the inhalator. Immediately beneath indicator dial 80 is proportion scale 81 on middle cylinder 39 which serves as a guide to obtaining fractional gas mixtures other than the mixtures obtained when the full areas of three portals are exposed.

Gas mixtures produced by the aperture positions illustrated in FIGS. 7 and 8 are marked by pointer settings 82' and 82", respectively. Setting 82" yields 66% $N_2O$ and 33% $O_2$; setting 82' yields 66% $CO_2$ and 33% oxygen; setting 82" yields 33% $CO_2$, 33% $N_2O$ and 33% $O_2$; and setting 82''', yields about 17% $CO_2$, 50% $N_2O$ and 33% $O_2$. Other settings will yield other proportions of $CO_2$ and $N_2O$ while maintaining the one-third proportion of $O_2$. Intermediate gas proportions of 55% $N_2O$ and 11% $CO_2$ can be obtained by setting the indicator one-third of the way between position 82 and position 82". Proportions of 44% $N_2O$ and 22% $CO_2$ are obtained at a position two-thirds of the way from 82 to 82". Further, a 44% $CO_2$ and 22% $N_2O$ proportion is obtained at a position one-third of the distance from 82" to 82', 50% $CO_2$ is obtained at the half-way mark, and 55% $CO_2$ is obtained at two-thirds the distance from 82" to 82'. Percentages intermediate to those marked on the dial 80 are obtained by interpolation and approximation which may be readily accomplished by inspection.

The aforementioned advantage of six gas cylinders can also be obtained by supplying gas to the six portals in the following order: the first and third portals are connected to $N_2O$; the second and fifth portals to oxygen; and the fourth and sixth portals to $CO_2$. Like the first arrangement, this arrangement has the advantage that full 360° rotation of the inner and outer inhalator cylinders, relative to each other, is possible.

Other ratios can be obtained by varying the number of gas supply circuits and portals, as well as the length of the regulating aperture, to yield, for example, three parts $CO_2$ and/or $N_2O$ to one part $O_2$.

A five portal arrangement for supplying the illustrative range of gas proportions is illustrated in FIG. 9. In this case, the first and second portals are connected to $N_2O$, the third portal to $O_2$, and the fourth and fifth portals to $CO_2$. A stop 78 is provided which extends from middle cylinder 39 into aperture 44 for stopping travel of inner cylinder 43 when stop 78 abuts against the edge of aperture 44. Mispositioning of the inhalator to produce a mixture of gases which does not include oxygen is thus avoided. As before, the length of regulating aperture 44 is sufficient to insure the full exposure of three portals at a time.

FIGS. 10-14 are views, in cross-section, of an embodiment of the invention which may be used in situations where the gas supply reserve afforded by duplication of gas supply circuits as shown in the embodiment of FIGS. 1-9, can be dispensed with. The proportion-regulating inner cylinder is shown in FIGS. 10-14 in five mixing positions. Here inhalator 160 has three portals and includes outer cylinder 162 and middle cylinder 164; like the structure of FIGS. 1-9, inhalator 160 contains paired inlet portals. Three demand valve inlet adapters 166, 167, and 168 are disposed at regular intervals, centered in a plane which is parallel to the bases of the cylinders. Inner end 169 of demand valve inlet adapter 168 extends beyond the inner surface of middle cylinder wall 164 and serves as a stop for limiting rotation of proportion control cylinder 170. As seen in FIGS. 10-14, the inner cylinder wall appears as three solid portions 170a, 170b, and 170c, and inner end 169 of adapter 168 extends into the aperture space between solid portions 170a and 170b. Like the inhalator of FIGS. 1-9, the inhalator of FIGS. 10-14 preferably consists of concentrically mounted, somewhat conical cylinders. Except for the details just described, the inhalator of FIGS. 10-14 generally conforms to the earlier construction. Three demand valves are provided (not shown) each of which is inserted in one of the inlet adapters 166, 167, and 168, and each of which is supplied, as before, with gas from its own, independent, gas supply circuit. The gases, for example oxygen, carbon dioxide and nitrous oxide, are supplied from pressurized supply cylinders via pressure reducing valve and gages as described above.

In this embodiment of the invention, the proportional control has three individual apertures 172, 174, and 176 which lie in the plane containing the centers of the inlet portals and which are separated by inner cylinder wall portions 170a, 170b and 170c. As may be seen by following the progression of solid wall portion 170c from position to position in FIGS. 10-14, the amount of carbon dioxide or nitrous oxide which can be admitted to central mixing space 172 can be varied from 50% to 0 and from 0 to 50%, respectively, while the supply of oxygen remains uninterrupted. FIG. 10 shows a 50% oxygen and 50% nitrous oxide mixture because carbon dioxide inlet 166 is blocked by a portion of inner cylinder 170c. When, as shown in FIG. 11, wall portion 170c is positioned so that inlet adapter 166 is partially uncovered, some carbon dioxide is admitted to the mixing space and the quantities of nitrous oxide via inlet adapter 167, and of oxygen admitted via inlet adapter 168 are reduced relatively; a 40% oxygen, 40% nitrous oxide, and 20% $CO_2$ mixture results. When solid wall portion 170c is further advanced, as shown in FIG. 12, the inner openings of all three inlet adapters 166, 167, and 168 are equally exposed to mixing space 172, and the mixture of gases obtained is composed of equal parts, or one third of each gas. Continuing the advance of solid wall portion 170c, FIG. 13 shows a condition in which the inner opening of inlet adapter 167 is partially closed, resulting in a 20% nitrous oxide, 40% carbon dioxide, and 40% oxygen mixture. Finally, in FIG. 14, the flow of nitrous oxide to mixing space 172 is completely shut off by solid wall portion 170c, and a 50—50 mixture of carbon dioxide and oxygen results. The presence of stop portion 169 of adapter 168 prevents rotation of inner cylinder 170 beyond the extreme positions of FIGS. 10 and 14 and, hence, the production of undesired mixtures. A continuous supply of oxygen to the patient is thus assured, while providing for variation, in therapeutically desirable ranges, of the nitrous oxide and carbon dioxide content of the mixture.

It is a further feature of the invention that the mixtures of gases supplied by the inhalator described above can be humidified for those patients whose pharyngeal and/or tracheal areas are sensitive to the dry atmosphere of gases supplied from compressed gas cylinders. FIG. 15 shows, in vertical cross-section, a humidifier 120 which may be used for this purpose with inhalators fabricated in accordance with the trackings of the invention.

Humidifier 120 includes a slightly conical, outer cylinder 122 which is preferably made of clear plastic and which is dimensioned so as to fit snugly into inner cylinder 43, being inserted, for example, about two inches into mixing chamber space 45 of inhalator 2. A close fit, which may be enhanced by gaskets (not shown), prevents admission of outside air via the interface between cylinders 43 and 122. Inner cylinder 124 is supported concentrically within outer cylinder 122 by means of transverse lower and upper end disks 126 and 128. The upper and lower edges of inner humidifier cylinder 124 are hermetically joined to the inner edges of upper and lower end discs 128 and 126 and the outer edges of the disks are sealed to the inner surface of outer humidifier cylinder 122, forming a toroidal humidification space. A water reservoir 132 is located at the bottom of this toroidal space. Gases mixed in mixing chamber 45, to which the upper end of humidifier assembly 120 is exposed, are led into water reservoir 132 by means of a plurality of vertical feeder tubes 134 which extend downward from the mixing space into the water in reservoir 132.

When the patient, whose mouth and nose are inserted into the lower end of the humidifier assembly, inhales, air is withdrawn from the toroidal humidification space. The humidified mixed gas is supplied to the patient from space 138 in inner cylinder 124, passing thereto via lateral apertures 140. Apertures 140 are placed well above humidifier water supply 132 and permit the mixed, moist gas to travel from the humidification space into central space 138. To separate entrained moisture from gas which has bubbled from the bottom of inlet tubes 134 through humidifier water supply 132, a pair of cylindrical barriers 142 and 144 are concentrically disposed about inner humidifier cylinder 124. Thus, incoming mixed gas first rises from the bottoms of tubes 134 through water reservoir 132 and travels upwards outside of outer separator 142 to arrive at a plurality of outer separator inlets 146. From inlets 146 the gas travels downward between outer barrier cylinder 142 and inner separation cylinder 144 to a second set of inlets 148 in inner separator 144. The flow of gas then reverses and rises to inlets 140 in innermost cylinder 124, whence it travels via inner space 138 to the patient. The series of reversals made by the gas as it travels up and down past the successive separation cylinders results in the removal of entrained moisture. The removed liquid gravitates downward into humidifier water reservoir 132. Submerged holes 150 in the bottom of the inner and outer separation cylinders provide free communication of liquid within the reservoir. During use of the humidifier, of course, the level of humidifying water 132 is maintained above lateral reservoir openings 150 as well as above the bottoms of feeder tubes 134.

When the patient exhales, the exhalation travels upwards in central air column 138 to one-way exhalation valve 152. This valve releases easily under this pressure, permitting the exhaled gas to travel directly into the mixing space in the inhalator and thence, as described above, out to the atmosphere through the side ports in the demand valves. Valve 152 closes automatically when the patient inhales. Instead of the illustrated, spring-loaded stop 156, one-way exhalation valve 152 may simply comprise a rubber flapper which is seated against cylindrical aperture in the end face which closes off central column 138.

Figure 3:
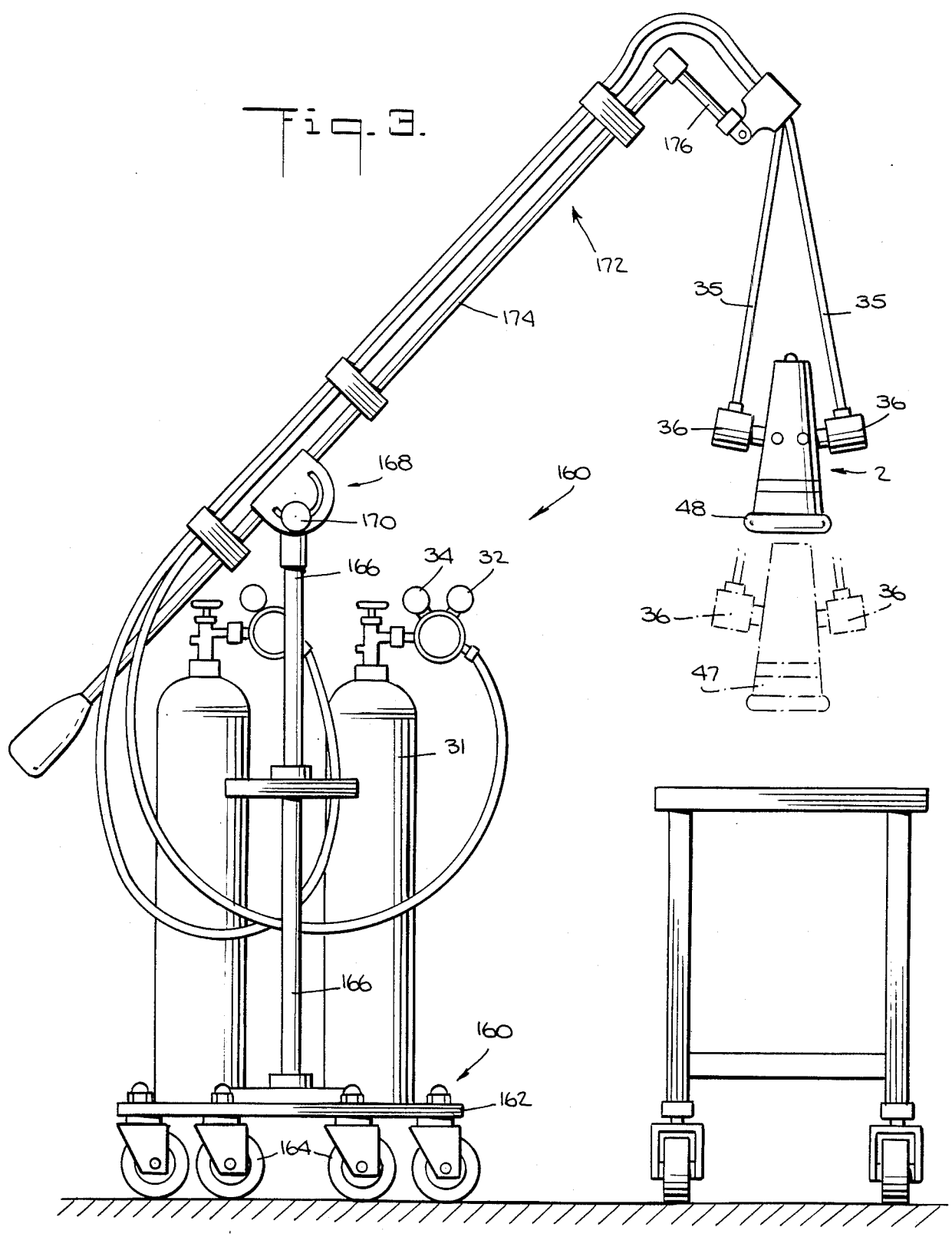
FIG. 3 is a pictorial representation of the apparatus of the invention and its transparent carriage, with the inhalator ready to be positioned over a patient.
Figure 4:
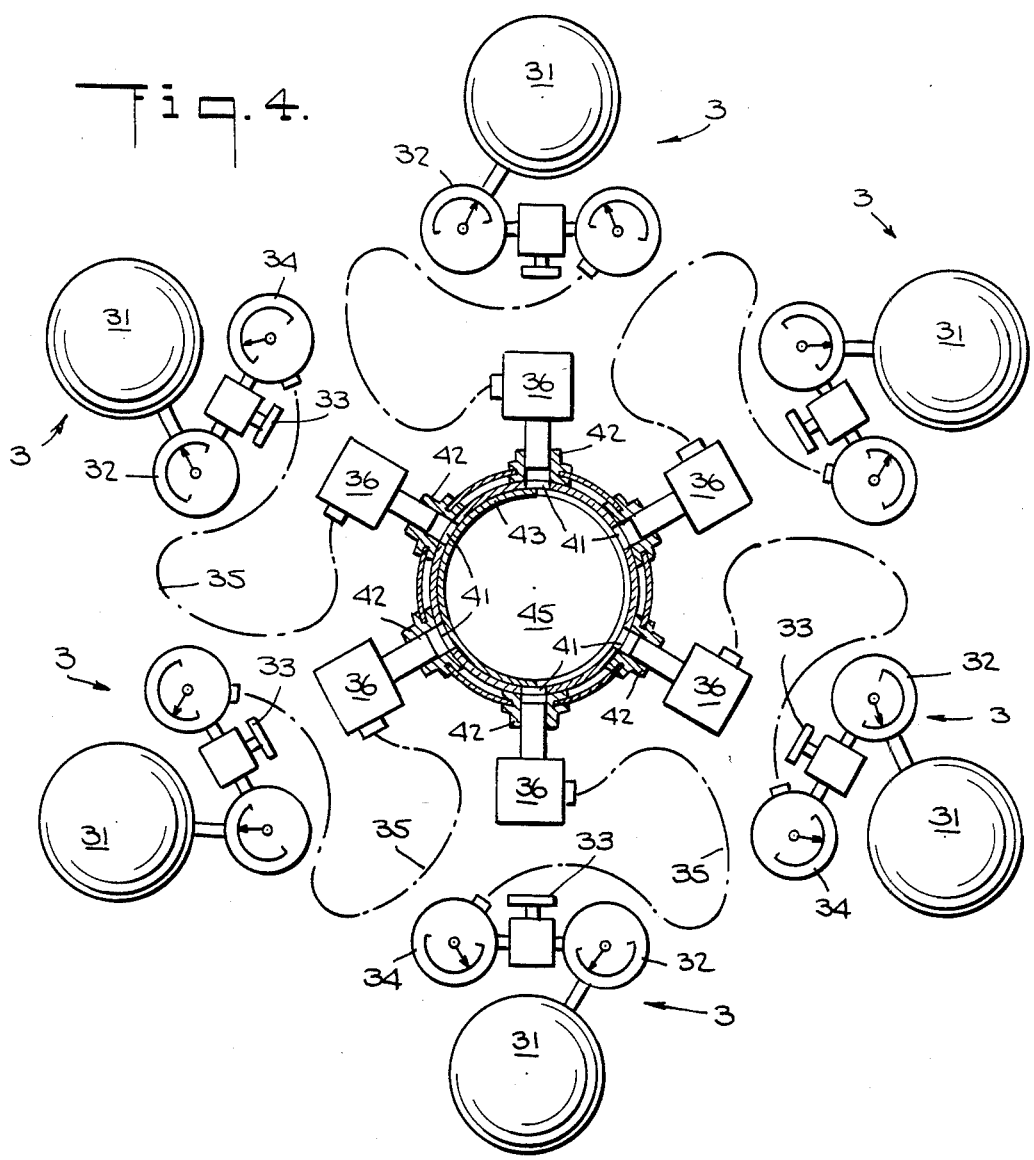
FIG. 4 is a horizontal view, in partial cross-section through the proportioning valve of FIG. 2, so as to show the six radially disposed input circuits.
Figure 5:
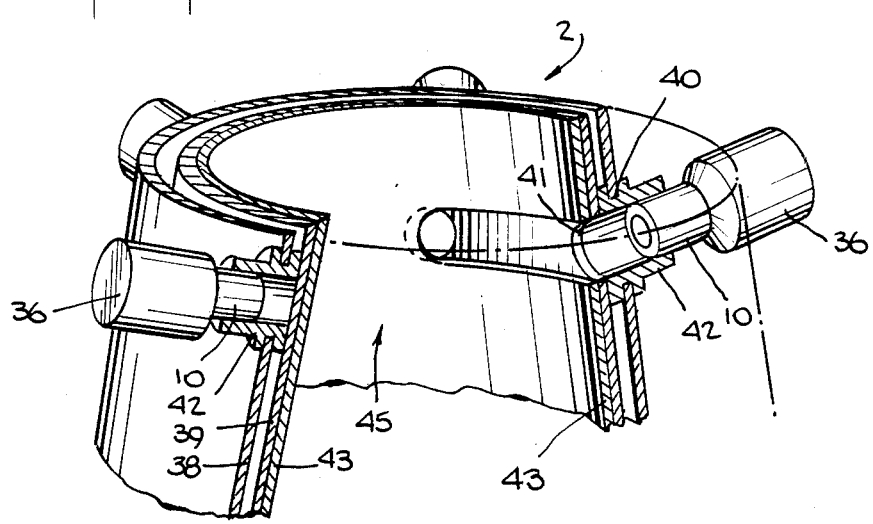
FIG. 5 is a partial side view, in cross-section, of the nested parts of the rotary proportioning valve of FIG. 2, showing the proportion-regulating aperture through which gases are admitted to the mixing chamber.

The general procedure for operation of the inhalator of FIGS. 1-9 is as follows. The inhalator is connected to the sources of gas and the demand valves are all adjusted to supply gas at the same demand pressure. The indicator dial is first set to deliver 67% nitrous oxide, 33% oxygen and 0% carbon dioxide to the patient. The inhalator can then be placed, on its suspension from movable boom 140 over the patient's head as shown in FIG. 3. The patient is reclining and the therapist, seated near the patient's head, lowers the inhalator and places the face cushion over the patient's nose and mouth with sufficient force to make a pneumatic seal. It will be understood that, depending upon the patient, the face adapter with its cushion may be attached to a humidifier, as shown in FIG. 10, or, in the case of patients who prefer the use of dry gases, directly to the bottom of inhalator 2. When the patient inhales, only those demand valves which are unblocked by the control aperture in the regulating inner cylinder wall of the inhalator will respond to the negative pressure to release gas into the mixing chamber. The gases flow into and are mixed in the mixing chamber and then pass to the patient. If one of the demand valves is only partially uncovered, that valve will release a lesser quantity of gas. When the patient exhales, the pressure in the mixing chamber is elevated and gas is released through the unblocked demand valves.

At the outset, the patient is usually given the mixture just described. As the treatment progresses, the therapist slowly rotates the outer assembly of the inhalator so as to decrease the nitrous oxide and increase the carbon dioxide. The oxygen level is maintained constant. This procedure may be continued until the patient is breathing 67% carbon dioxide, 33% oxygen and no nitrous oxide. Frequently a mixture of one-third oxygen, one-third nitrous oxide, and one-third carbon dioxide is therapeutically adequate. The patient normally hyperventilates as he begins breathing higher concentrations of carbon dioxide. The inhalator of the invention is capable of meeting the resulting increase in demand for volume flow of gas for any individual because ample quantities of the mixed gas can be supplied on demand and because of the low impedance to the flow of gas to the patient which is presented by the mixing inhalator and the humidifier attachment, when it is used.

Continued breathing of the mixture results in the patient losing consciousness. When this occurs, the inhalator and face cushion are lifted off of the patient's face, allowing the patient to recover consciousness and to resume a normal breathing rate.

The procedure may be repeated at the discretion of the therapist after a short rest period. By means of the invention the therapist is able to instantaneously regulate the proportions of nitrous oxide and carbon dioxide by changing the regulator indicator setting, all the while maintaining a life-supporting flow of oxygen at a more than adequate level.

It will be apparent to those skilled in the art that the embodiments of the invention described above are susceptible to substantial variation without departing from the teachings of the invention. The below-appended claims are, therefore, to be interpreted in keeping with the spirit of the invention, rather than limited to the illustrative structures.

What is claimed is:

1. A proportional mixing inhalator for mixing and supplying a mixture of at least three therapeutic gases to a patient while maintaining the proportion of at least one of the gases at a life-sustaining level, the inhalator comprising:

first body means comprising a wall surface penetrated by at least three inlet portals;

demand valve means having outlets coupled, respectively, to each inlet portal and having inlets for receiving, respectively, one of the gases to be mixed, each demand valve means responsive to a decrease in pressure level at its outlet to deliver gas through the outlet;

second body means comprising a wall surface conformably fitted to the wall surface of the first body means and movable relative thereto, the second body means comprising a mixing chamber;

aperture means in the wall surface of the second body means, the aperture means communicating with the mixing chamber and movable with the wall surface of the second body to close off inlet portals in the first body means, the aperture means and the portals being so disposed that at least one inlet portal to which the one gas is coupled can not be completely closed off, while the portals to which the remaining gases are coupled can be partially or fully closed off; and means for delivering mixed gas from the mixing chamber to the nose and mouth of the patient.

2. The inhalator of claim 1 in which the conformably contacting surfaces of the first and second body means are surfaces of revolution and in which the inlet portals and the aperture means are movable circumferentially, relative to each other.

3. The inhalator of claim 1 in which there are at least five inlet portals and five demand valve means, and further comprising:

at least three sources of gas, each source being coupled to at least one demand valve means.

4. The mixing valve of claim 3 in which one of the sources is a source of oxygen which is coupled to one demand valve means.

5. The inhalator of claim 1 and further comprising:

stop means mounted on one of the body means, the stop means interacting with the other body means to limit travel of the aperture means relative to the inlet portals.

6. The inhalator of claim 1 in which there are an even number of inlet portals and demand valve means, the number being greater than two, and in which each of the demand valve means is coupled to one of at least three different sources of gas.

7. The inhalator of claim 1 in which five demand valve means are coupled to five inlet portals to supply gas from sources of gas of three different kinds, in the following sequence:
the first and second inlet portals supplied with gas of a first kind;
the third inlet portal supplied with gas of a second kind; and
the fourth and fifth inlet portals suppled with gas of a third kind.

8. The inhalator of claim 1 in which six demand valve means are coupled to supply gas from sources of gas of three kinds to six inlet portals in the following sequence:
the first and second inlet portals supplied with gas of a first kind;
the third inlet portal supplied with gas of a second kind;
the fourth and fifth inlet portals supplied with gas of a third kind; and
the sixth inlet portal supplied with gas of the second kind.

9. The inhalator of claim 1 in which six demand valve means are coupled to supply gas from sources of gas of three kinds to six inlet portals as follows:
the first and third inlet portals supplied with gas of a first kind;
the second and fifth inlet portals supplied with gas of a second kind; and
the fourth and sixth portals supplied with gas of a third kind.

10. The inhalator of any one of claim 7, 8 or 9 in which the gas of the second kind is oxygen.

11. The inhalator of claim 7, 8 or 9 in which the gas of the first kind is nitrous oxide, the gas of the second kind is oxygen, and the gas of the third kind is carbon dioxide.

12. The inhalator of claim 1, for use in mixing three therapeutic gases, in which there is an inlet portal and an associated demand valve for each gas and in which the aperture means comprises an aperture for each portal.

13. The inhalator of claim 12 having three inlet portals in a first body and having three corresponding regulating apertures in a second body which enables regulation and proportioning of gases by rotation of the first body around the second body thereby permitting:
(a) the three input gases to mix in variable proportions according to the areas of the various inlet portals which are unblocked by the second body because of passing through the proportioning apertures and thereby communicating directly with the mixing chamber;
(b) gradual exclusion of either of two gases alternatively; and
(c) inability to exclude one gas, oxygen.

14. The inhalator of any one of claim 12 or 13 in which the one gas is oxygen.

15. The inhalator of claim 14 in which the other two gases are nitrous oxide and carbon dioxide.

16. The inhalator of claim 1 and further comprising: means for supporting the inhalator in position over the nose and mouth of the patient.

17. The inhalator of claim 1 and further comprising:
means for sustaining the weight of the inhalator when the inhalator is in place on the face of the patient, the means for sustaining the weight comprising a boom and a boom support, the boom having an end from which the inhalator is suspended, the boom being movable on the support to position the inhalator.

18. The inhalator of claim 1 in which the means for delivering mixed gas comprises a wide transparent tube enclosing the nose and mouth of the patient.

19. The inhalator of claim 1 and further comprising:
a rubber inflatable cushion on the means for delivering mixed gas for effectively sealing the inhalator around the nose and mouth of the patient.

20. The inhalator of claim 1 and further comprising:
a humidifier coupled to the mixing chamber and having a low impedance outlet for delivering humidified, mixed gases from the inhalator to the patient.

21. The inhalator of claim 20 in which the humidifier further comprises:
reservoir means for a humidifying liquid;
low impedance means for passing gas from the mixing chamber into a humidifying liquid in the reservoir; and
means for removing condensed and entrained moisture from humidified gas emerging from the reservoir prior to delivery to the patient.

22. The inhalator of any one of claim 20 or claim 21 comprising:
exhalation valve means in the humidifier responsive to a gas pressure level at the low impedance outlet which is greater than the pressure level in the mixing chamber for returning gas exhaled by the patient directly to the mixing chamber without passing through the reservoir.

23. The inhalator of claim 1 and further comprising dial means for indicating the proportional amounts of the gases being mixed in said mixing chamber, said dial means including a pointer on one of said first body means and said second body means and a scale on the other of said first body means and said second body means.

24. A rotary gas-proportioning inhalator for supplying a mixture of therapeutic gases to a patient while maintaining the supply of oxygen to the patient at a life-sustaining level, the inhalator adapted to be supported over the nose and mouth of the patient, the inhalator comprising:
a first substantially cylindrical hollow container having a side wall, a closed end, and an open end;
a second substantially cylindrical hollow container comprising a mixing chamber having a side wall, a closed end, and an open end;
the second container nested in the first container with its closed end juxtaposed to the closed end of the first container;
means for maintaining the nested relationship of the cylinders while permitting rotation of the cylinders relative to one another about a common axis;
at least three inlet portals in the side wall of the first container, the inlet portals centered in a plane which lies perpendicular to the axis of rotation;
a demand valve in each of the inlet portals, each demand valve having an outlet potentially connected to the mixing chamber and having an inlet for receiving gas, each unblocked demand valve responsive to a decrease of the pressure in the mixing chamber to a predetermined level to admit gas thereto;

a source of gaseous oxygen connected to the inlet of at least a first demand valve;

a source of gaseous carbon dioxide connected to the inlet of at least a second demand valve;

a source of nitrous oxide connected to the inlet of at least a third demand valve;

at least one aperture in the wall of the second hollow container which provides continuous exposure to the mixing chamber of at least one portal which is connected to a source of oxygen while providing, by rotation of the cylinders relative to one another, variation from zero to full exposure to the mixing chamber of at least one portal which is connected to a source of carbon dioxide simultaneously with variation from full to zero exposure of at least one portal which is connected to the source of nitrous oxide;

a substantially cylindrical transparent adapter to be mounted on the open end of the second hollow container, the adapter having a circular end spaced from the open end of the hollow container upon a mounting of the adapter thereto; and engagement means including a substantially annular face cushion attached to the circular end of the adapter for engaging the face of a patient and forming a substantially air-tight seal therewith in a substantially circular region about the patient's nose and mouth.

25. The rotary gas proportioning inhalator of claim 24 and further comprising:

a substantially cylindrical humidifier conformably fitted in the open end of the second hollow container, the humidifier comprising an open end projecting away from the inhalator, the open end being adapted with a face cushion to receive the face of the patient.

26. The rotary gas proportioning inhalator of claim 24 in which there are only three inlet portals and in which the wall of the second container has three apertures, each aperture comprising an elongate opening for one inlet portal, the long dimension of each opening lying in the plane of the inlet portals, and further comprising:

a stop for limiting rotational travel of the apertures to prevent cut-off of the portal connected to the oxygen source.

27. The rotary gas proportioning inhalator of claim 24 in which there are six inlet portals spaced at equal distances around the first hollow cylinder, and in which the aperture comprises a single opening which extends half way around the wall of the second container exposing at least three of the portals at a time.

28. Apparatus for supplying a mixture of therapeutic gases to a patient comprising a rotary gas proportioning inhalator in accordance with claim 24 and further comprising:

means for movably supporting the inhalator comprising a transport carriage, a support pole on the transport carriage, and an adjustable boom on the support pole, the inhalator being suspended at the end of the boom.

29. A proportional mixing inhalator for mixing and supplying a mixture of three therapeutic gases to a patient while maintaining the proportion of at least one of the gases at a life-sustaining level, the inhalator comprising:

first body means comprising a wall surface penetrated radially by at least three inlet portals;

second body means comprising a wall surface conformably fitted to the wall surface of the first body means and rotatable relative thereto about an axis of rotation, the second body means comprising a mixing chamber;

aperture means including at least one elongate opening extending in a circumferential direction in the wall surface of the second body means, said three inlet portals and said elongate opening being disposed in a common plane oriented perpendicularly to said axis of rotation, the aperture means communicating with the mixing chamber and movable with the wall surface of the second body to open and close off inlet portals in the first body means, the aperture means and the portals being so disposed that at least one inlet portal to which the one gas is coupled can not be completely closed off, while the portals to which the remaining gases are coupled can be partially or fully closed off to feed the remaining gases to said mixing chamber in reciprocally variable proportions;

multiple demand valve means having a plurality of inlets each for receiving, respectively, one of the gases to be mixed and further having outlets coupled to each inlet portal, respectively, each demand valve means responsive to a decrease in pressure level at its outlet to deliver gas to said mixing chamber through the outlet when the outlets communicates with the mixing chamber;

pressure-regulating means for providing the three therapeutic gases to the inlets of the demand valve means at substantially the same pressure; and means for delivering mixed gas from the mixing chamber to the nose and mouth of the patient.

* * * * *